US007560487B2

(12) United States Patent
Bertini et al.

(10) Patent No.: US 7,560,487 B2
(45) Date of Patent: Jul. 14, 2009

(54) USE OF (R)—IBUPROFEN METHANESULFONAMIDE AND SALTS THEREOF IN THE TREATMENT AND PREVENTION OF REJECTION REACTIONS OF TRANSPLANTED ORGANS

(75) Inventors: Riccardo Bertini, L'Aquila (IT); Francesco Colotta, L'Aquila (IT); Roberto Novellini, Milan (IT)

(73) Assignee: Dompé Pha.r.ma S.p.A., L'Aquila (IT)

( * ) Notice: Subject to any disclaimer, the term of this patent is extended or adjusted under 35 U.S.C. 154(b) by 0 days.

(21) Appl. No.: 10/250,465

(22) PCT Filed: Jan. 30, 2003

(86) PCT No.: PCT/EP02/00946

§ 371 (c)(1), (2), (4) Date: Oct. 2, 2003

(87) PCT Pub. No.: WO02/062330

PCT Pub. Date: Aug. 15, 2002

(65) Prior Publication Data

US 2004/0102520 A1      May 27, 2004

(30) Foreign Application Priority Data

Feb. 2, 2001   (IT) .......................... MI2001A0206

(51) Int. Cl.
*A61K 31/195*   (2006.01)
*A61K 31/16*   (2006.01)

(52) U.S. Cl. ...................................... 514/562; 514/600
(58) Field of Classification Search ................ 514/600, 514/562
See application file for complete search history.

(56) References Cited

U.S. PATENT DOCUMENTS 4,879,283 A * 11/1989 Belzer et al. ................ 435/1.2
6,355,682 B1 * 3/2002 Weinberg ................... 514/562

FOREIGN PATENT DOCUMENTS

WO      WO 00 24710 A      5/2000

OTHER PUBLICATIONS

Li et al., Transplantation Proceedings, vol. 32, No. 7, pp. 2531-2534 (2000).

* cited by examiner

*Primary Examiner*—Jennifer M Kim
(74) *Attorney, Agent, or Firm*—Birch, Stewart, Kolasch & Birch, LLP

(57) ABSTRACT

The use of (R)-ibuprofen methanesulfonamide is described for the preparation of medicaments for the treatment and prevention of functional injury resulting from rejection reactions of transplanted organs.

In particular, the use of non-toxic salts of (R)-ibuprofen methanesulfonamide, such as the (L)-lysine salt, is described for the prevention and the treatment of rejection reactions of transplanted kidneys.

7 Claims, 1 Drawing Sheet

Figure 1. Data are mean ± SD.☐range values of serum creatinine in control animals receiving a syngeneic graft not exposed to cold ischemia (control non ischemic).

USE OF (R)—IBUPROFEN METHANESULFONAMIDE AND SALTS THEREOF IN THE TREATMENT AND PREVENTION OF REJECTION REACTIONS OF TRANSPLANTED ORGANS

This application is the national phase under 35 U.S.C. § 371 of PCT International Application No. PCT/EP02/00946 which has an International filing date of Jan. 30, 2002, which designated the United States of America.

The present invention relates to the use of (R)-ibuprofen methanesulfonamide and non-toxic salts thereof for the preparation of medicaments for the treatment and prevention of functional injury resulting from rejection reactions of transplanted organs.

BACKGROUND OF THE INVENTION

Organ transplantation, especially of renal type, has made substantial strides in the past few decades, with the introduction of improved immunosuppressive regimens, organ preservation, and pre- and postoperative care. Nevertheless, there is considerable room for improvement, particularly in terms of improving long-term outcome. Initial ischemia/reperfusion injury occurring secondary to organ retrieval, storage, and transplantation has been associated with subsequent deterioration and transplant failure. In renal transplantation the absence of immediate allograft function is known as delayed graft function (DGF) which is commonly and broadly defined as the need of dialysis during the first week after transplantation. Delayed graft function is the most common allograft complication in the immediate posttransplant period, affecting up to 50% of primary cadaveric renal transplants (Ojo A O et al. *Delayed graft function: risk factors and implications for renal alloagraft survival. Transplantation* 63, 7:968-974, 1997; Koning O H J et al. *Risk factors for delayed graft function in cadaveric kidney transplantation. Transplantation* 63, 11:1620-1628, 1997). Although different etiologies may cause DGF of implanted allograft, there is accumulating experimental and clinical evidence suggesting that post-ischemic reperfusion injury to allograft may represent the major key event responsible for the occurrence of DGF. There is unanimous agreement that the combination of DGF and early rejection is a severe indicator of poor graft survival and that the occurrence of DGF leads to an increased risk of acute rejection (Carmellini M et al. *Delayed graft function adversely affects one-year graft survival of cadaveric renal transplants. Transplant Proc* 28, 1.359-360, 1996). The pathogenesis of ischemia/reperfusion injury is now known to involve cytokines and particularly surface adhesion molecules, the expression of which initiates the attachment of inflammatory cells. Evidence from experimental animals with acute renal ischemia has shown that the intercellular adhesion molecule-1 (ICAM-1) is promptly up-regulated after injury and that neutrophil, T cell, and macrophage infiltrations subsequently occur. Interleukin-8 (IL-8), a cytokine with a potent chemotactic effect for polymorphonuclear cells (PMN), can be generated by the activation of endothelial cells that follows reperfusion and may contribute to the complex events ultimately leading to delayed graft function due to ischemia/reperfusion injury. Recently, new compounds that selectively inhibit the biological activity of IL-8 have been discovered. Among these, R (–)-N-[2-(4-Isobutylphenyl)propionyl]-methanesulfonamide, hereinafter referred to as (R)-ibuprofen methanesulfonamide, and its L-lysine salt (hereinafter referred to as DF 1681B), have been described in international patent application WO 00/24710 as selective in vitro inhibitors of the chemotaxis of neutrophils induced by IL-8 and therefore desirably suitable for the treatment of neutrophil-dependent pathologies.

DF 1681B has now been shown to inhibit chemotaxis in vivo in a mouse model and to inhibit PMN infiltration in different models of ischemia/reperfusion injury in mice and rats.

Indeed, according to the current state of the art, the selective inhibition of IL-8-induced chemotaxis is not a sufficient condition for the protection of a transplanted organ from functional injury. In fact, the scientific literature identifies numerous factors involved in the etiology of the delay in functional recovery of the transplanted kidney, among which factors, IL-8 does not certainly appear as one of the most important: for example, IL-8, together with IL-3 and soluble CD 23, (Kutukculer N. et al., *Transplantation*, 1995, 59(3), 333-40) is reported to be of no diagnostic use for organ rejection given that, in any case, high levels of these markers were also present in transplant patients who were wholly free from rejection phenomena. Moreover, in addition to IL-3, IL-8 and CD 23, scientific literature identifies various other possible pro-inflammatory molecules as possible pathogenetic factors of the delay in the functional recovery of the transplanted organ, such as, for example, IL-1beta, IL-2, IL-10, IL-17, MIP-1beta, MCP-1, etc. It follows that, from the literature data, an aspecific inhibitor of the inflammatory response or, at the least, of leukocyte recruitment would appear necessary for the inhibition of reperfusion injury in organ transplantation, especially that of kidneys.

DESCRIPTION OF THE INVENTION

It has now surprisingly been found out that, contrary to any expectations from the prior art discussed above, (R)-ibuprofen methanesulfonamide and its lysine salt (L-lysine or DL-lysine) are effective in the protection from functional injury in organ transplantation, particularly that of kidneys. Moreover, the same compounds were shown to be active in the prevention of ischemia/reperfusion injury.

Such an activity has been demonstrated in an experimental model of kidney transplantation in rats, disclosed in detail herein after, in which DF 1681B proved active in the preservation of renal function immediately after ischemia/reperfusion injury which follows syngeneic kidney transplantation, also preventing leukocyte infiltration in the transplant which occurs following post-ischemic reperfusion.

Adult male Lewis rats (RT11) (Charles River, Calco Italia S.p.A, Italy) were used. All animals were allowed free access to food and water. The study was performed in a syngeneic kidney transplant model using such rats as donor and graft recipients. Donor animals were anaesthetized with leptofen. The left kidney was prepared by freeing the ureter from the attachments. The renal artery was separated from the renal vein by dissection. The donor kidney and ureter were removed "en bloc" and flushed with Belzer (UW) containing 1000 U/ml of heparin. Then the kidney was placed in an iced Belzer (UW) solution for 4-6 hours (cold ischemia) until transplant. Recipients were prepared by removal of the left kidney. Animal treatment with DF 1681B is summarized below. Kidney grafts were washed with saline solution before transplant. An anastomosis was created between the recipient and the donor renal artery as well as renal vein with end-to-end anastomosis. Vascular clamps were released after 30 minutes (warm ischemia). Donor and recipient ureters were attached end-to-end. The native right kidney was then removed. Animals were placed in individual metabolic cages for measurements of daily urine output as an index of renal function recovery. After 16 and 24 hours, renal function was assessed by measuring plasma creatinine concentration. Twenty-four hours after kidney transplantation, the animals were sacrificed. The kidney graft was removed, cut in slices and put in Dubosq-Brazil solution for the analysis of conventional histology by light microscopy. Moreover, additional kidney fragments were frozen in liquid nitrogen and used for immunohistochemical analysis of inflammatory cell infiltrate (polymorphonuclear cells, MHC class II positive cells).

The following experimental groups of animals were considered:

Group 1 (n.=3) rats recipients of a kidney graft exposed to 4 hours cold ischemia and treated with the IL-8 inhibitor DF 1681B.

Group 2 (n.=3) rats recipients of a kidney graft exposed to 4 hours cold ischemia and treated with the vehicle.

Group 3 (n.=3) rats recipients of a kidney graft exposed to 6 hours cold ischemia and treated with the IL-8 inhibitor DF 1681B.

Group 4 (n.=3) rats recipients of a kidney graft exposed to 6 hours cold ischemia and treated with the vehicle.

The recipients were pretreated the day before the experiment (15 mg/kg s.c.). The animals received an intravenous injection of DF 1681B (15 mg/kg) immediately before reperfusion of the transplanted kidney. Additional administration of the compound (15 mg/kg s.c.) was performed 2 hours after transplantation. Control animals were given vehicle at the same time points and using the same administration method as for animals treated with DF 1681B.

In addition, DF 1681B proved active in the preservation of renal function immediately after ischemia/reperfusion injury which follows kidney allotransplantation. The following experimental group of animals were considered:

Group 1 (n=9) Brown Norway rats recipients of a kidney graft of Lewis rats exposed to 6 hours cold ischemia and treated with vehicle.

Group 2 (n=5) Brown Norway rats recipients of a kidney graft of Lewis rats exposed to 6 hours cold ischemia and treated with the IL-8 inhibitor DF 1681B.

The recipients were pretreated the day before the experiment (20 mg/kg s.c.). The animal received an intravenous injection of DF 1681B (20 mg/kg) immediately before reperfusion of the transplanted kidney. Additional administration of the compound (20 mg/kg s.c.) was performed 2 hours after transplantation. Control animals were given vehicle at the same time points and using the same administration method as for animals treated with DF 1681B.

Data were analyzed using the non-parametric Kruskal-Wallis test for multiple comparisons or the Tukey-Cicchetti test.

BRIEF DESCRIPTION OF THE FIGURE

FIG. 1 and table 1 show plasma creatinine concentrations in Lewis rats at 16 and 24 hours after receiving a syngeneic kidney transplant, pre-exposed to 4 and 6 hour cold ischemia. In animals receiving 4 hour ischemic kidneys, plasma creatinine increased after surgery reaching values that at 16 and 24 hours were significantly higher than values observed in a control group of animals receiving a non-ischemic syngeneic kidney transplant. Treatment with DF 1681B protected animals from renal function deterioration, the values of plasma creatinine at 24 hours being fairly comparable to those of animals receiving a non-ischemic syngeneic kidney transplant (table 2). As expected, 6 hours ischemia induced a more severe renal function impairment, as documented by significantly higher plasma creatinine levels than in animals receiving a syngeneic kidney transplant after 4 hour ischemia (figure and table 1). DF1681B significantly reduced plasma creatinine concentrations to levels that, however, were still significantly higher than those measured in animals receiving a non-ischemic syngeneic kidney transplant.

Figure 1:
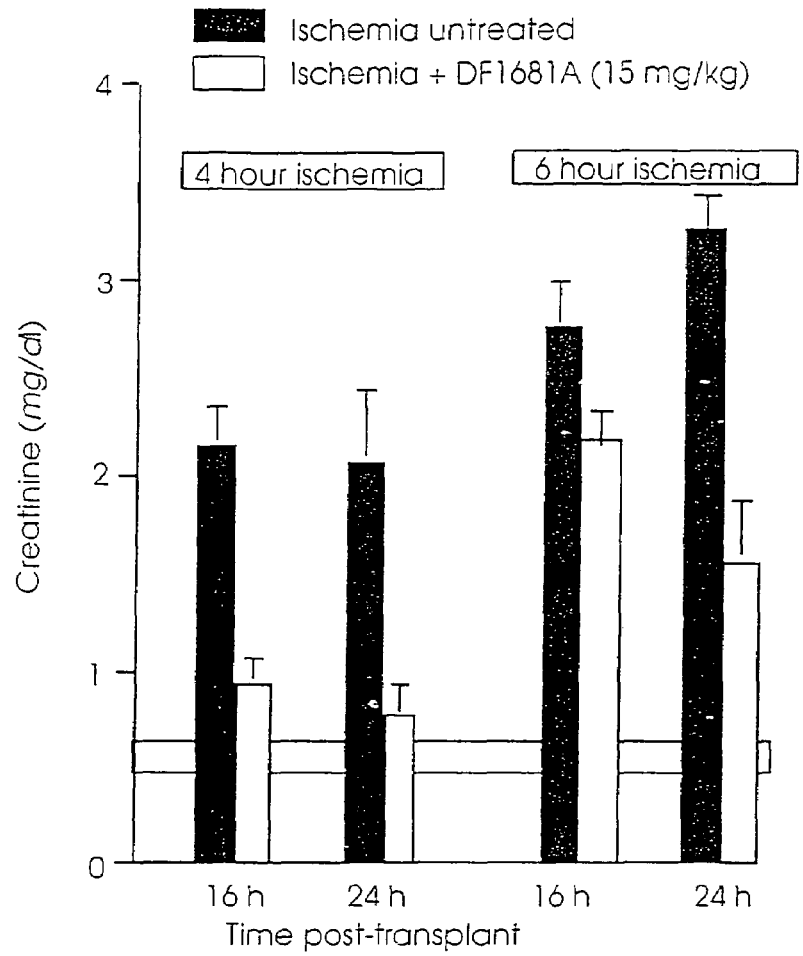
FIG. 1 shows results.

Detailed immunohistologic evaluation of leukocyte infiltration in transplanted kidney, studied at 24 hours post-transplant, is summarized in table 2. In kidneys undergoing 4 hour cold ischemia a large number of granulocytes was found in the interstitium and, to a lesser extent, in intra and periglomerular areas. The compound decreases the PMN infiltrate and attenuates the tubular variations induced by ischemia/reperfusion. Granulocyte count in the intraglomerular area was numerically but not significantly lowered by the IL-8 inhibitor. The cellular infiltrates did not consistently increase after 6 hour ischemia compared to values after 4 hour ischemia. Again, interstitial inflammatory cells were significantly lowered ($p<0.01$) by DF 1681B. With respect to neutrophils, the number of MHC class II cells was lower in kidneys transplanted following 4 and 6 hour ischemia. Cells were detected mainly in the interstitium (table 3) and their number was not affected by the IL-8 inhibitor.

Histologic scores of glomerular, interstitial and tubular injury observed in sections from kidneys transplanted after 4 and 6 hour cold ischemia and studied 24 hours after transplantation are shown in table 4. By light microscopy transplanted kidneys were characterized by degenerative changes of tubular epithelial cells predominantly in proximal tubuli, manifested by cell swelling, vacuolization and necrosis (table 4). DF 1681B attenuated but did not normalize tubular changes after 4 hour ischemia. In addition, tubular casts were found in all kidneys. Focal ischemic changes were detected in the glomeruli only in kidneys exposed to 6 hour ischemia and they were prevented by DF 1681B.

DF 1681B is thus able of preventing renal function impairment secondary to cold ischemia. The compound reduces the number of cellular infiltrates and attenuates tubular changes induced by ischemia. Data have been confirmed in other animals. 6 hour ischemia induces a very severe renal function impairment.

The effect of DF 1681B on serum creatinine concentrations in Brown Norway rats at 16 and 24 hours after receiving an allogeneic kidney transplant from Lewis rats is shown in Table 5. A significant prevention of increased serum creatinine levels was observed consistently in all rats receiving 20 mg/kg of the treatment.

The above data clearly show how (R)-ibuprofen methanesulfonamide or its lysine salt (L-lysine or DL-lysine) can be advantageously used in medical practice.

For this purpose, (R)-ibuprofen methanesulfonamide or its lysine salt will be suitably formulated in pharmaceutical compositions which may be administered in oral, parenteral, rectal or topic route, before and after transplantation surgery. Examples of suitable formulations include capsules, tablets, suppositories, syrups, drops, suspensions, emulsions, injectable sterile solutions, vials of sterile lyophilized powders for injection, controlled release formulations, transdermal formulations, ointments and the like. The techniques and carriers used for the preparation of such formulations are wholly conventional, as described for example in Remington's Pharmaceutical Sciences Handbook, Mack Pub. Co., New York, USA, XVII Ed.

The pharmaceutical formulations are to be preferably administered in unit dosage forms containing from 1 to 500 mg, more preferably from 10 to 100 mg, of (R)-ibuprofen methanesulfonamide or the equivalent of its lysine salt.

Higher doses can also be considered, depending on the circumstances. The administration can be a single one or divided into more administrations spread over a suitable time period, normally from some day before surgery until some weeks afterwards. (R)-Ibuprofene methanesulfonamide or an acceptable salt thereof, such as lysine salt can, if necessary, be administered in combination with others drugs of complementary or, in any case, useful action, for instance anti-inflammatory agents, immunosuppressants, analgesics, antithrombotic agents.

EXAMPLE 1

Preparation of R-ibuprofen-methanesulfonamide

A suspension of R(−)-2-(4-Isobutylphenyl)-propionic acid (R-ibuprofen, 4 g, 0.019 mol) in thionyl chloride (7.4 mL) was refluxed for 4 h; then left to cool spontaneously at r.t.

The thionyl chloride in excess was evaporated off under vacuum.

The last traces of thionyl chloride were removed washing twice the residual mass with a few drops of dry dioxane and evaporating the solvent under vacuum. 4.66 g (0.019 mol) of R(−)-2-(4-Isobutylphenyl)-propionyl chloride were obtained as yellow oil, which was dissolved in a few ml of anhydrous tetrahydrofuran (THF).

Separately, methanesulfonamide (2.3 g, 0.0243 mol) was added to a suspension of potassium tert-butoxide (2.73 g, 0.0244 mol) in anhydrous THF (28 mL) and the mixture was stirred for 30 min at r.t. After that, the solution of R(−)-2-(4-Isobutylphenyl)-propionyl chloride (4.66 g, 0.019) as obtained above was added under stirring, keeping the reaction mixture stirred overnight at r.t.

The separated inorganic salts were filtered off, the solvent was evaporated off under vacuum and the oily residue was partitioned between $CH_2Cl_2$ (30 mL) and a monosodium phosphate saturated solution. The organic phase was washed with water (2×10 mL) and the aqueous phases were extracted with $CH_2Cl_2$ (2×10 mL). The combined organic extracts were dried over $Na_2SO_4$ and the solvent was evaporated off, then the solution of the oily residue in anhydrous MeOH (10 mL) was added with two micro-drops of concentrated sulfuric acid, to esterify to methyl ester any traces of untransformed R(−)-2-(4-Isobutylphenyl)-propionic acid. The mixture was kept overnight at r.t., the solvent was cautiously evaporated under vacuum, the residue was partitioned between water (10 mL) and methylene chloride (25 mL). The aqueous phases were discarded and the organic phase was extracted with a $NaHCO_3$ saturated solution (2×20 mL). The basic phases were combined, acidified with conc. HCl and extracted with $CH_2Cl_2$ (3×15 mL). After the usual washings to neutrality, the combined organic extracts were dried over $Na_2SO_4$ and the solvent was evaporated off under vacuum to obtain 1.86 g (0.0066 mol) of R(−)-N-[2-(4-Isobutylphenyl)propionyl]-methanesulfonamide: m.p. 103-105° C. (dec.); $[\alpha]_D=-68$ (c=1; $CH_3OH$); $^1$H-NMR (DMSO-$d_6$) δ 7.3 (d, 2H J=8 Hz); 7.09 (d, 2H J=7 Hz); 3.42 (q, 1H, J=8 Hz); 2.8 (s, 3H); 2.45 (d, 2H, J=7 Hz); 1.55 (m, 1H); 1.3 (d, 3H, J=8 Hz), 0.95 (d, 6H, J=7 Hz).

EXAMPLE 2

Preparation of R-ibuprofen-methanesulfonamide L (+)-lysine salt (DF 1681B)

A solution of L(+)-lysine (129 mg; 0.88 mmol) in water (1.3 mL) was added to a solution of R(−)-N.[2-(4-Isobutylphenyl)propionyl]-methanesulfonamide (250 mg; 0.88 mmol) in 1 ml of methanol. The solvent was evaporated off and the residual mass was taken up with ethyl ether (5 mL) and stirred overnight at room temperature. The crystalline, highly hygroscopic material which separated was filtered quickly under nitrogen atmosphere, washed on the filter with anhydrous ethyl ether and dried under vacuum at 50° C. for 2 h to give 360 mg of R(−)-N-[2-(4-Isobutylphenyl)propionyl]-methanesulfonamide salt of L(+)-lysine as pale yellow powder. $[\alpha]_D=-17.3°$ (c=1.15; $CH_3OH$); $^1$H-NMR ($D_2O$): δ7.30 (dd, 4H, J=8 Hz), 3.77 (t, 1H, J=7Hz), 3.65 (q, 1H, J=7 Hz), 3.05 (m, 5H), 2.52 (d, 2H, J=7 Hz), 1.92 (m, 2H), 1.75 (m, 2H), 1.50 (m, 3H), 1.40 (d, 3H, J=7 Hz), 0.90 (6H, d, J=7 Hz).

TABLE 1

"Effect of DF1681B on serum creatinine in rats receiving syngeneic kidney transplant"

| Rat | Group | Plasma Creatinine (mg/dl) | |
| --- | --- | --- | --- |
| | | 16 h | 24 h |
| 10 gr 1 | Vehicle (4 h) | 2.27 | 2.58 |
| 11 | | 1.82 | 1.14 |
| 12 | | 2.24 | 2.49 |
| 13 | | 2.30 | 2.09 |
| | | 2.16 ± 0.23* | 2.08 ± 0.66* |
| 1A | DF1681B (4 h) | 1.09 | 0.99 |
| 2A | | 0.74 | 0.64 |
| 3A | | 0.89 | 0.71 |
| | | 0.91 ± 0.18° | 0.78 ± 0.19° |
| 2D | Vehicle (6 h) | 2.76 | 2.91 |
| 3D | | 2.39 | 3.64 |
| 4D | | 3.58 | 3.27 |
| | | 2.91 ± 0.61** | 3.27 ± 0.37** |
| 1E | DF1681B (6 h) | 2.32 | 1.89 |
| 2E | | 2.54 | 1.87 |
| 3E | | 1.84 | 1.72 |
| | | 2.23 ± 0.36*Δ | 1.83 ± 0.09# |
| | Range Control (non ischemic syngeneic kidney) | 0.5-0.6 | |

Data are expressed as mean ± SD
*p < 0.05,
**p < 0.01 vs Control
°p < 0.05 vs Vehicle 4 h
p < 0.05 vs Vehicle 6 h
Δp < 0.05 vs DF1681 4 h

TABLE 2

"Effect of DF1681B on the number of granulocytes counted in at least 10 randomly selected high-power microscopic fields (X400) for each animal".

| Rat | Granulocytes | | | | |
| --- | --- | --- | --- | --- | --- |
| | Intraglom | Periglom. | Intravasc. | Perivasc. | Inrterstitial |
| 10gr1 Vehicle (4 h) | 6.2 ± 6 | 4 ± 4 | 0.3 ± 1 | 10 ± 6 | 21.6 ± 11 |
| 11 | 4.7 ± 4.4 | 5.3 ± 3.4 | 1.7 ± 2.9 | 9.7 ± 9.9 | 25.8 ± 11.6 |
| 12 | 18.1 ± 20.2 | 7.6 ± 8.1 | 15 ± 14.8 | 12 ± 7 | 39.8 ± 29.9 |

TABLE 2-continued

"Effect of DF1681B on the number of granulocytes counted in at least 10 randomly selected high-power microscopic fields (X400) for each animal".

| Rat | | Intraglom | Periglom. | Intravasc. | Perivasc. | Inrterstitial |
|---|---|---|---|---|---|---|
| 13 | | 33 ± 11.3 | 74.3 ± 43.9 | 9.4 ± 7.2 | 48 ± 29 | 135.7 ± 31.5 |
| | | 15.5 ± 13.1 | 22.8 ± 34.4 | 6.6 ± 6.9 | 19.9 ± 18.7 | 55.7 ± 53.9 |
| 1A | DF1681B (4 h) | 7.4 ± 4.7 | 5.3 ± 4.5 | 1.5 ± 2.4 | 3 ± 0.8 | 9.1 ± 6.4 |
| 2A | | 14 ± 15.4 | 4 | 0 | 8 ± 2.6 | 11 ± 4.8 |
| 3A | | 7 ± 2.9 | 7 ± 8 | 8 ± 5.3 | 5.3 ± 4.6 | 16.2 ± 8.3 |
| | | 9.5 ± 3.9 | 5.4 ± 1.5 | 3.2 ± 4.3 | 5.4 ± 2.5* | 12.1 ± 3.7* |
| 2D | Vehicle (6) | 10.4 ± 5.8 | 7.3 ± 4.3 | 3.3 ± 2.0 | 5.8 ± 3.3 | 25.4 ± 22 |
| 3D | | 12.3 ± 9.5 | 2.9 ± 1.1 | 1.4 ± 2.1 | 5.6 ± 2.7 | 23.6 ± 18 |
| 4D | | 10.5 ± 7.6 | 2.8 ± 2.1 | 0 | 1.3 ± 2.3 | 23.1 ± 6.0 |
| | | 11.1 ± 1.1 | 4.3 ± 2.6 | 1.6 ± 1.7 | 4.2 ± 2.5 | 24 ± 1.2 |
| 1E | DF1681B (6 h) | 5.0 ± 6.0 | 1.0 ± 1.8 | 0.2 ± 0.4 | 1.0 ± 1.3 | 2.5 ± 4.6 |
| 2E | | 3.7 ± 3.0 | 3.2 ± 1.9 | 0 | 6.8 ± 8.9 | 4.8 ± 5.6 |
| 3E | | 7.7 ± 6.5 | 2.2 ± 1.2 | 3.0 ± 4.0 | 4.5 ± 4.4 | 1.6 ± 1.2 |
| | | 5.5 ± 2.0° | 2.1 ± 1.1 | 1.1 ± 1.7 | 4.1 ± 2.9 | 3 ± 1.7° |

Data are expressed as mean ± SD.
*p < 0.05 vs. Vehicle 4 h
°p < 0.05 vs. Vehicle 6 h

TABLE 3

"Effect of DF1681B on the number of MHC II positive interstitial cells counted in at least 10 randomly selected high-power microscopic fields (×400) for each animal".

| Rat | | MHC II+ |
|---|---|---|
| 10 gr 1 | Vehicle (4 h) | 11.5 ± 7 |
| 11 | | 16.6 ± 5 |
| 12 | | 7.7 ± 2.8 |
| 13 | | 12.8 ± 7.2 |
| | | 12.2 ± 3.7 |
| 1A | DF1681B (4 h) | 5.1 ± 6.2 |
| 2A | | 9.1 ± 2 |
| 3A | | 11.9 ± 6.3 |
| | | 8.7 ± 3.4 |
| 2D | Vehicle (6 h) | 6.9 ± 2 |
| 3D | | 17.3 ± 8.9 |
| 4D | | 21.3 ± 3.6 |
| | | 15.2 ± 7.4 |
| 1E | DF1681B (6 h) | 10.5 ± 4.7 |
| 2E | | 13.1 ± 7 |
| 3E | | 19.7 ± 3.3 |
| | | 14.4 ± 4.7 |

Data are expressed as mean ± SD.

TABLE 4

"Semi-quantitative score for renal damage"

| | | Histological damage | | |
|---|---|---|---|---|
| Rat | | Glomerular (score) | Interstitial (score) | Tubular (score) |
| 10 | Vehicle (4 h) | 0 | 2 | 1.3 |
| 11 | | 0 | 2 | 1 |
| 12 | | — | — | — |
| 13 | | 0 | 3 | 0.7 |
| | | 0 | 2.3 ± 0.6 | 1 ± 0.3 |
| 1A | DF1681B (4 h) | 0 | 2.5 | 1.5 |
| 2A | | 0 | 2 | 0.7 |
| 3A | | 0 | 2 | 0.5 |
| | | 0 | 2 ± 0.3 | 0.7 ± 0.6 |
| 2D | Vehicle (6 h) | 1 | 2 | 1.33 |
| 3D | | 1 | 2.5 | 1.33 |

TABLE 4-continued

"Semi-quantitative score for renal damage"

| | | Histological damage | | |
|---|---|---|---|---|
| Rat | | Glomerular (score) | Interstitial (score) | Tubular (score) |
| 4D | | 1 | 2.5 | 1.2 |
| | | 1 | 2.3 ± 0.3 | 1.3 ± 0.1 |
| 1E | DF1681B (6 h) | 0 | 3 | 1.7 |
| 2E | | 0 | 3 | 1.7 |
| 3E | | 0 | 3 | 1.2 |
| | | 0 | 3 | 1.5 ± 0.3 |

Data are expressed as mean ± SD.

TABLE 5

"Effect of DF1681B on serum creatinine in rats receiving allogeneic kidney transplant".

| | | Plasma Creatinine (mg/dl) | |
|---|---|---|---|
| Brown Norway Rat | Group | 16 h | 24 h |
| 1T | Vehicle | 1.4 | 1.74 |
| 2T | | 1.27 | 1.20 |
| 3T | | 0.82 | 0.96 |
| 4T | | 2.23 | 2.28 |
| 5T | | 2.67 | 2.67 |
| 6T | | 2.23 | 2.29 |
| 7T | | 1.66 | 2.37 |
| 8T | | 1.67 | 1.6 |
| 9T | | 1.86 | 1.9 |
| Mean ± | | 1.76 | 1.86 |
| sd | | 0.56 | 0.59 |
| 1Z | DF1681B | 1.05 | 1.3 |
| 2Z | | 1.2 | 1.39 |
| 3Z | | 1 | 0.87 |
| 4Z | | 0.84 | 0.69 |
| 5Z | | 1.01 | 0.85 |
| Mean ± | | 1.02 | 1.02 |
| sd | | 0.12 | 0.3 |

The invention claimed is:

1. A method of preserving renal function in connection with a syngeneic kidney transplant in a patient, comprising administering to said patient prior to, during and/or after said transplant in said patient (R)-ibuprofen methanesulfonamide, or a non-toxic salt thereof in an amount effective to preserve renal function.

2. The method according to claim 1, wherein the non-toxic salt is the L-lysine or DL-lysine salt.

3. The method according to claim 2, wherein the non-toxic salt is the L-lysine salt.

4. The method of claim 1, wherein said (R)-ibuprofen methanesulfonamide or a non-toxic salt thereof is administered in oral, parenteral, rectal or topical routes, before and/or after transplantation surgery.

5. The method of claim 4, wherein said (R)-ibuprofen methanesulfonamide or a non-toxic salt thereof is in the form of a capsule, tablet, suppository, syrup, drop, suspension, emulsion, injectable sterile solution, sterile lyophilized powder for injection, controlled release formulation, transdermal formulation or ointment.

6. The method of claim 4, wherein said (R)-ibuprofen methanesulfonamide or a non-toxic salt thereof is administered in a dosage of 1 to 500 mg.

7. The method of claim 4, wherein said (R)-ibuprofen methanesulfonamide or a non-toxic salt thereof is administered in a single or multiple dose.

* * * * *

UNITED STATES PATENT AND TRADEMARK OFFICE
CERTIFICATE OF CORRECTION

| | | |
|---|---|---|
| PATENT NO. | : 7,560,487 B2 | Page 1 of 1 |
| APPLICATION NO. | : 10/250465 | |
| DATED | : July 14, 2009 | |
| INVENTOR(S) | : Riccardo Bertini et al. | |

It is certified that error appears in the above-identified patent and that said Letters Patent is hereby corrected as shown below:

Title page, item (22) should read:

(22)   PCT Filed:   Jan. 30, ~~2003~~ 2002

Signed and Sealed this

Fifth Day of January, 2010

David J. Kappos
*Director of the United States Patent and Trademark Office*